United States Patent [19]

Mayer et al.

[11] 4,125,500
[45] Nov. 14, 1978

[54] CYCLIC PHOSPHITES OF SUGAR ALCOHOLS AND POLYMERS STABILIZED THEREWITH

[75] Inventors: Norbert Mayer, Gersthofen; Gerhard Pfahler, Augsburg; Franz Scheidl, Gersthofen, all of Fed. Rep. of Germany

[73] Assignee: Hoechst Aktiengesellschaft, Frankfurt am Main, Fed. Rep. of Germany

[21] Appl. No.: 818,123

[22] Filed: Jul. 22, 1977

[30] Foreign Application Priority Data

Jul. 24, 1976 [DE] Fed. Rep. of Germany ....... 2633393

[51] Int. Cl.$^2$ .......................... C08K 5/52; C08B 37/00
[52] U.S. Cl. ................................. 260/23 H; 252/407; 260/23 XA; 260/45.8 A; 260/45.8 R; 260/45.95 R; 536/117
[58] Field of Search ................. 260/45.8 A, 45.7 PH, 260/45.7 P, 927 R, 982, 937, 403, 402.5, 399, 928, 30.6, 45.95 R, 23 XA, 23 H; 536/117; 252/407

[56] References Cited

U.S. PATENT DOCUMENTS

| | | | |
|---|---|---|---|
| 2,265,585 | 12/1941 | Urbain et al. | 260/927 R |
| 3,082,189 | 3/1963 | Mack et al. | 260/937 |
| 3,103,507 | 9/1963 | Knoevenagel | 536/117 |
| 3,287,299 | 11/1966 | Canarios | 260/982 |
| 3,382,236 | 5/1968 | Guttag | 536/117 |
| 3,459,835 | 8/1969 | Dever et al. | 260/927 R |
| 3,472,919 | 10/1969 | Nagy et al. | 536/117 |
| 3,652,743 | 3/1972 | Harris et al. | 260/982 |

*Primary Examiner*—V. P. Hoke
*Attorney, Agent, or Firm*—Connolly and Hutz

[57] ABSTRACT

The invention is related to novel phosphites of sugar alcohols, their use as stabilizers for organic polymers, furthermore to stabilizer compositions containing these novel phosphites as well as the organic polymers stabilized therewith.

The novel phosphites have a good stabilizing effect, especially in combination with known stabilizers, and they are substantially stable against hydrolytical influence. Their volatility and tendency to exudation are very weak.

6 Claims, No Drawings

CYCLIC PHOSPHITES OF SUGAR ALCOHOLS AND POLYMERS STABILIZED THEREWITH

It is known that during the processing of synthetic polymers organic phosphites are added as co-stabilizers in addition to other stabilizers. Most of these commercial phosphite esters are liquids, for example, tris-nonylphenyl phosphite. Since the other plastic stabilizers are generally solids, liquid phosphite esters, when added to the plastics powders, require special dosage installation. In many cases, the liquid additives impair the mechanical properties of plastics materials. For example, if commercial liquid phosphites are added to rigid PVC, the so-called Vicat-value, i.e. the temperature at which the plastics material begins to soften, is reduced in undesired manner. With polyolefins, the addition of liquid phosphites may often lead to the, equally very undesired, stress cracking corrosion.

These problems have been known for a long time; it is, therefore, not surprising that also solid phosphites have been described in the literature as stabilizers, for example esters of long chain alcohols with the branched polyol pentaerythritol (U.S. Pat. No. 2,961,454). A commercial stabilizer of this group is distearyl-pentaerythritol diphosphate which, however, has the great disadvantage of causing discolorations if added during processing of PVC, so that it gained some importance in the processing of polyolefins only. Even phosphite esters of the heterocyclic polyol anhydro-enneaheptite (U.S. Pat. No. 3,326,939) have been proposed, but have hitherto not yet been used in practice.

In addition, the hitherto known solid phosphites show a generally disadvantageous property, which is also latent with liquid phosphites, i.e. their great susceptibility to hydrolysis. This susceptibility is not so important with the liquid phosphites, since, as liquids, they have naturally a small specific surface and are stored in general in closed vessels which are tight to the access of atmospheric humidity. The solid phosphites, on the other hand, must be brought on the market in the form of flowable powders or flakes for reasons of better dosage. The large specific surface of the fine-grained phosphites considerably facilitates the attack of the omnipresent atmospheric humidity. In addition, the material from which the bags are made, which are used for the packing of the solid phosphite stabilizers, are by far not so tight to humidity as the containers for liquids. It is, therefore, understandable that the usual solid phosphite stabilizers are reduced in their activity, caused by hydrolysis upon prolonged storage.

It is the object of the present invention to provide solid phosphite stabilizers for synthetic plastic materials which have an improved stability to hydrolysis.

Now, we have found that, surprisingly, stabilizers which meet these requirements in exellent manner are mixed esters of phosphorus-containing acids, unbranched open chain sugar alcohols and long chain alkyl compounds which contain a functional group with one active hydrogen atom.

Accordingly, the present invention relates to compounds of the formula

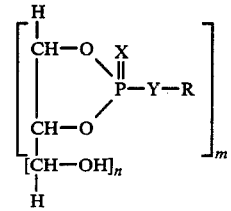

in which
$m = 2$ or 3,
$n = 0$, 1 or 2 and $2m + n$ is equal to or lower than 6,
$Y = $ —O—, —S— or —NR'— with R' = H or $C_1$ to $C_{20}$-alkyl, preferably —O—,
$X = $ 0 or preferably no substituent,
$R = a$ preferably unbranched alkyl radical of 12 to 30 carbon atoms or a mono- or di-fatty acid ester of the dihydroxypropyl radical, the fatty acid having a chain length of 12 to 20 carbon atoms.

The invention furthermore relates to a process for the manufacture of these esters as well as to their use as stabilizers for plastics materials.

The polyol compounds on which the substances of the invention are based are open-chain sugar alcohols having 4 to 6 carbon atoms, such as erythritol, adonitol, arabitol, dulcitol, but preferably xylitol and, in particular sorbitol and mannitol.

By long chain alkyl compounds which contain a functional group with an active hydrogen atom, there are to be understood monohydric alcohols and mercaptans as well as primary and secondary monoamines. Suitable alcohols are, for example, fatty alcohols and wax alcohols with a chain length of 12 to about 30 carbon atoms, preferably 12 to 25 carbon atoms, as those which can be obtained by the hydrogenation of fatty acids and wax acids, which are contained in natural and fossil waxes, or synthetic alcohols produced from ethylene by oligomerization and traded under the name "Alfols". In this respect, stearyl and behenyl alcohol are preferred components. Other preferred alcohol components are glycerol mono- or di-fatty acid esters, the fatty acid component of which contains 12 to 20 carbon atoms, in particular glycerol mono- and di-stearate or the commercial mixture of these two substances. In some cases it is of advantage to add the alcohol component in an excess of 5 to 15%. As mercaptans, those containing 12 to 30, preferably 12 to 20 carbon atoms, are used, preferably octadecyl- and, above all, dodecyl-mercaptan. Suitable amines contain 12 to 30 carbon atoms, for example laurylamine, stearylamine, N-methylstearylamine or also distearylamine.

The mixed esters of the invention are obtained by trans-esterification of tri-lower alkyl phosphites or phosphates or triphenyl-phosphite or -phosphate with the above-mentioned substances. The presence of inert solvents, for example toluene, xylene or carbon tetrachloride during the trans-esterification is possible, but generally does not bring any advantage.

The trans-esterification reaction can be catalyzed by basic substances such as alkali metal hydroxides, alkali metal alcoholates, alkali metal amides, alkyl amines or preferably di- and tri-alkylamines such, for example as 2,2,6,6-tetramethyl-4-hydroxypiperidine or triethylamine, added in a quantity of 0.01 to about 5%, referred to the weight of the reaction batch.

The reaction temperature is in general between about 60° and 250° C., preferably between 80° and 200° C. In general, it is chosen in such a manner as to permit good separation by distillation of the alcohol set free. It is possible, of course, and advantageous in the case of higher boiling alcohols such as phenol, to facilitate the separation of the alcohol by reducing the pressure.

A special advantage is that the compounds of the invention can be obtained by a "one-pot"-reaction. The sugar alcohol, the derivative of phosphorous acid or, if desired, of phosphoric acid with easily volatile alcohol or amine substituents which can be split off by hydrolysis, for example $P[N(CH_3)_2]_3$, or preferably a phosphite ester or phosphate ester of easily volatile alcohols, for example tripropyl phosphite or triphenyl phosphite and especially trimethyl or triethyl phosphite, and the long chain alcohols, amines or mercaptans or a mixture of these substances are introduced into the reaction vessel, then one of the mentioned basic catalysts is added and the substituent of the phosphorus-containing acid set free by alcoholysis is removed by distillation.

Of course, it is also possible to react only the sugar alcohol and the phosphorous acid ester to the corresponding sugar alcohol phosphite esters, the manufacture of which has already been described (c.f. Voskresenskaja, P. A. Kirpienikov and E. T. Mukmenev, Isvest. Akad. Nauk. SSSR, Ser. Chim., 1970, 7, 1666–1668) and then to synthetize in a second reaction step by the addition of corresponding molar amounts of fatty alcohols, fatty amines or -mercaptans and removal by distillation of the equivalent amounts of easily volatile alcohol set free to obtain the phosphites of the invention, for example according to the reaction scheme:

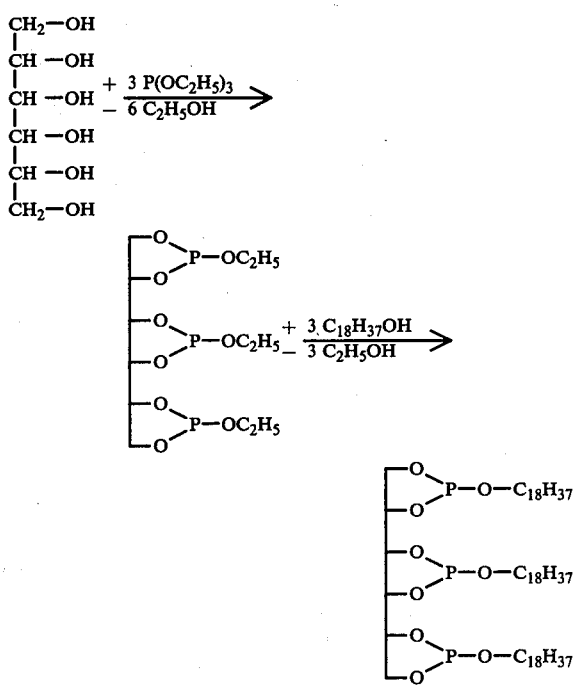

These two esterification steps can also be carried out in reverse direction without disadvantage.

The above-mentioned "one-pot"-process is in many cases advantageous, especially if the intermediate compound obtained in the two-step process is a highly viscous phase at the reaction temperature which can be hardly stirred and thus be handled with difficulty only.

The esters of the invention have the "formal" structure indicated in the general formula, which means that this formula just shows the gross composition of the respective substance, but does not give any details on the position of the phosphite ester linkage on the sugar alcohol molecule and on the mutual spatial arrangement of the substituents to one other.

The general formula furthermore shows that the invention does not only encompass the fully esterified sugar alcohol phosphites or phosphates, but also partially esterified phosphites or phosphates with up to two free OH-groups. Such compounds may have in some cases advantages over the fully esterified sugar alcohol phosphites or phosphates. The invention furthermore encompasses, in addition to the compounds in which all radicals —Y—R— contained in the molecule are identical, also compounds with different —Y—R— substituents, for example two oxyalkyl groups and one thioalkyl group.

The products of the invention obtained in this or in another way constitute easily motile liquids with low viscosity above the melting point, can be easily filtered and solidify upon cooling to wax-like solids having melting points of about 40° to about 100° C. An advantage of the substances of the invention is the fact that they need not be subjected to an expensive and complex purification. On the other hand, this condition makes it understandable that the products obtained are not in every case chemically uniform and may contain by-products.

The esters of the invention have proved to be physiologically clean, as far as could be tested on some of them. Physiological tolerance is of great importance for a plastics additive, because the risk that poisons are introduced, for example over the packaging material, into foodstuffs, etc. is excluded solely if practically not-poisonous substances are used. The phosphites tested had in general an $LD_{50}$ of more than 5000 mg/kg of body weight, determined on mice, and no deaths occured even with the highest dose. Thus, according to the classification given by W. S. Spector in the "Handbook of Toxicology", these phosphites must be considered as being "practically not poisonous".

In PVC, the esters of the invention have an increased stability to discoloration as compared to pentaerythritol diphosphite derivatives. This fact is surprising and not forseeable. In contradistinction to pentaerythritol, the sugar alcohols have H-atoms in $\beta$-position to the oxygen substituent, so that elimination reactions with separation of phosphorous acid derivatives and formation of conjugated or even cumulated double bonds under extreme thermic conditions during the processing of the plastics material could have expected. It is known that highly unsaturated compounds of this type react with one another with the formation of deep brown to black resins. It is really surprising that this phenomenon does not occur, on the contrary, in practice the sugar alcohol phosphite compounds of the invention yield compositions which have in part a distinctly better or at least an equal color stability as compared to compositions with pentaerythritol phosphite derivatives.

Moreover, with the esters of the invention the processing stability of moldable compositions, especially on the basis of PVC, can be greatly improved. As shown in the Examples, the esters of the invention are distinctly superior to commercial products with regard to this property. This effect, too, is extremely surprising with regard to the aforesaid structural and chemical reasons and could not have been foreseen.

Finally, it is surprising and could by no means have been foreseen that the esters of the invention have a considerably better stability to hydrolysis than distearyl-pentaerythritol disphosphite. As compared to pentaerythritol diphosphite derivatives, the phosphite esters of pentites and hexites are expected to have a higher polarity and, hence, a higher sensitivity to hydrolysis considering the higher number of hydroxyl groups in the molecule. It is extremely surprising that, contrary to all expectations, the hydrophily is in part greatly reduced.

The esters of the invention are also very efficient in the stabilization of polyolefins. The addition of a usual amount thereof (less than 1% by weight) to polypropylene considerably improves the stability to light and heat, especially in the presence of phenolic and optionally sufidic antioxidants.

Phenolic and sulfidic stabilizers are intended to include the heat stabilizers generally used in plastics processing, for example 3,5-di-tert.butyl-4-hydroxyphenyl-propionic acid esters, 2,5-ditert.butyl-p-cresol, alkylidene-bis-alkylphenols, esters of bis(4'-hydroxy-3'-tert.butylphenyl)-butanoic acid or thiodipropionic acid esters of fatty alcohols or dioctadecyl sulfide and disulfide.

The esters of the invention are generally used as stabilizers in an amount of from 0.05 to 5 parts by weight, preferably 0.1 to 3 parts by weight for 100 parts by weight of polymer to be stabilized.

A stabilizer combination having a synergistic effect in the processing of halogen-free poly-α-olefins, for example high, medium and low pressure polymers of $C_2$ to $C_4$-α-olefins, especially polyethylene and polypropylene, or of copolymers of such α-olefins, consists, for example, of 0.05 to 3 parts by weight of a phenolic stabilizer, 0.05 to 2 parts by weight of the calcium salt of a fatty acid or a wax acid (such as stearic acid or montanic acid), optionally 0.1 to 3 parts by weight of a sulfidic stabilizer and 0.05 to 5, preferably 0.1 to 3 parts by weight of one or several esters of the invention, for 100 parts by weight of polymer. If necessary, 0.01 to 3 parts by weight of a special UV stabilizer can be added to the mixture. From among the great number of commercial UV stabilizers the following are named by way of example: alkoxyhydroxy-benzophenones, hydroxyphenyl-benztriazoles, salicylic acid phenyl esters, benzoic acid hydroxyphenyl esters, benzylidene-malonic acid mononitrile esters and so-called quenchers such as nickel chelates, hexamethyl-phosphoric acid triamide or piperidine stabilizers known as hindered amine light stabilizers (HALS products).

An addition of the esters of the invention, besides metal compounds known as stabilizers, epoxide stabilizers and optionally polyhydric alcohols, improves the heat and light stability not only in polyvinyl chloride processing but generally of chlorine-containing polymers such as chloropolyethylene or chlorine-containing vinyl homo- and copolymers, for example polyvinylidene chloride, polyvinyl chloroacetate and vinyl chloride-α-olefin copolymers.

Metal compounds known as stabilizers in this context are calcium, barium, strontium, zinc, cadmium, magnesium, aluminum and lead soaps of aliphatic carboxylic acids or hydroxycarboxylic acids having approximately 8 to 32 carbon atoms, preferably 8 to 20 carbon atoms, or of phenol-substituted aliphatic carboxylic acids, salts of the said metals with aromatic carboxylic acids preferably having 7 to 12 carbon atoms, for example benzoates, salicylates and (alkyl)-phenolates with alkyl radicals having from 1 to 12, preferably 1 to 6, carbon atoms. Further compounds of this type are organo-tin compounds, for example dialkyl-tin thioglycolates and carboxylates and optionally neutral and basic lead salts of inorganic acids such as sulfuric acid and phosphoric acid.

Known epoxide stabilizers are, for example, epoxidized higher fatty acids such as epoxidized soybean oil, tall oil or linseed oil, and epoxidized butyl oleate and the epoxides of long-chain α-olefins.

Suitable polyhydric alcohols are, for example, pentaerythritol, trimethylol propane, sorbitol, or mannitol, i.e. preferably alcohols having 5 or 6 carbon atoms and 3 to 6 hydroxyl groups.

A suitable stabilizer combination for the processing of halogen-containing polymers, for example chlorinated polyolefins or chlorine-containing vinyl homo- and copolymers, consists, for example, of 0.05 to 5 parts by weight of one of the esters of the invention, 0.1 to 10 parts by weight of metal compounds known as stabilizers, 0.1 to 10 parts by weight of a known epoxide stabilizer and 0 to 1 part by weight of a polyhydric alcohol, for 100 parts by weight of polymer.

Mixture of the esters of the invention with known stabilizers improve not only the stability of polyolefins and compositions on the basis of polyvinyl chloride but also of polyesters, polyamides, phenol-formaldehyde resins, epoxide resins, polystyrene, polyacrylonitrile, polycarbonates, polysiloxanes, polyethers, polyurethanes and SBR rubber mixtures.

The following examples illustrate the invention.

EXAMPLE 1

Tri-stearyl-sorbityl triphosphite (a) Two-stage process

In a 2 liter three-necked flask with stirrer, gas inlet tube, 15 cm Vigreux column and distillation bridge 182 g (1 mol) of dry sorbitol 560 ml (3.25 mols) of triethyl phosphite and 1 ml of triethylamine were stirred at 120° C. while passing through dry nitrogen. After approximatively 1 hour the development of ethanol started. The bath temperature was then regulated in a manner such that the outlet temperature of the distillation bridge did not exceed the boiling temperature of ethanol (78° C.). About 320 ml of ethanol (~ 6 mols) distilled over. When the ethanol distillation was terminated, 815 g (3 mols) of stearyl alcohol were added, whereupon the development of ethanol started again and about 165 ml thereof passed over (~ 3 mols). When the reaction was terminated, water jet vacuum was applied for about 30 minutes at a bath temperature of 200° C. in order to remove unreacted triethyl phosphite from the reaction mixture. The molten product remaining behind in the flask was filtered through a folded filter. After cooling, 1,080 g of a white brittle substance melting at 52° to 56° C. were obtained

| $C_{60}H_{119}O_9P_3$ | calculated | found |
|---|---|---|
| C | 66.9% | 67.5% |
| H | 11.1% | 11.4% |

In the infrared spectrum of the substance there were observed, besides absorptions at 1,030 to 1,050 cm$^{-1}$, which are characteristic of P-O-C linkages, bands at 1,250 to 1,300 cm$^{-1}$ which indicate the presence of P=O groups.

(b) One-stage process

At the beginning of the reaction 815 g (3 mols) of stearyl alcohol were additionally introduced into the reaction flask. After distillation of about 475 ml of ethanol, 1,061 g of a product melting at 51° to 53° C. were obtained.

EXAMPLE 2

Tri-stearyl-mannityl-triphosphite

Under the conditions of Example 1b) 995 g of a white brittle substance melting at 50° C.

| $C_{60}H_{119}O_9P_3$ | calculated | found |
|---|---|---|
| C | 66.9% | 67.3% |
| H | 11.1% | 11.5% | were prepared from 1 mol = 182 g of mannitol, 3 mols = 650 ml of triethyl phosphite, 3 mols = 815 g of stearyl alcohol, in the presence of 5 g of 2,2,6,6-tetramethyl-4-hydroxy-piperidine.

A product prepared according to the two-stage process of Example 1a) melted at 54° to 59° C.

EXAMPLE 3

Tri-stearyl-dulcityl-triphosphite

The compound was prepared under the conditions of Example 1(a) or (b) from dulcitol, stearyl alcohol and triethyl phosphite in the presence of triisopropyl amine. It melted at 50° to 53° C.

EXAMPLE 4

Tri-behenyl-sorbityl triphosphite

This compound melting at 58° C. was prepared under the conditions of Example 1b) using 3 mols = 1,116 g of behenol ($C_{22}H_{45}OH$) instead of stearyl alcohol.

EXAMPLE 5

Tri-behenyl-mannityl triphosphite

This compound was prepared under the conditions of Example 4 using mannitol. It had a melting point of 61° C.

The reaction products of Examples 1 to 5 have the formal structure

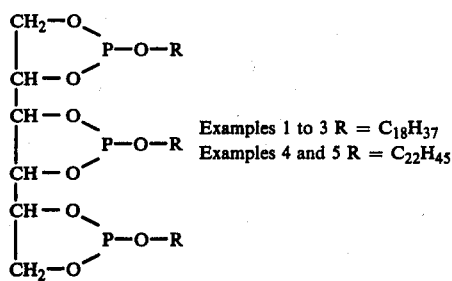

Examples 1 to 3 R = $C_{18}H_{37}$
Examples 4 and 5 R = $C_{22}H_{45}$

EXAMPLES 6 and 7

Instead of stearyl alcohol or behenol there can also be used as alcohol component industrial grade glycerol monostearate, i.e. a mixture consisting of about 55% of glycerol monostearate, 35% of glycerol distearate and 10% of glycerol tristearate and having a hydroxyl number of 242, corresponding to an equivalent weight of about 232 for each hydroxyl group.

By reacting 1 mol of sorbitol with 3 mols of triethyl phosphite and 700 grams of industrial grade glycerol monostearate (corresponding to 3 mols OH-groups) 933 g of a white solid melting at 57° C. were obtained.

The corresponding mannitol derivative melted at 53° C.

EXAMPLE 8

Di-behenyl-erythrityl diphosphite

Under the conditions of Example 1
122 g (1 mol) of erythritol,
374 ml (2 mols) of triethyl phosphite,
744 g (2 mols) of behenol, and
1 ml of triethyl-amine
were reacted, while distilling of the ethanol set free, whereby 904 g of a white substance melting at 67° C. were obtained.

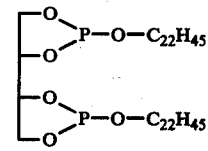

EXAMPLES 9 to 16

Compounds of the formula

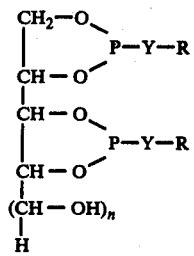

were prepared as specified in Example 1 by reacting 1 mol of sugar alcohol with 2 mols of trialkyl phosphite and 2 mols of alcohol component.

| Example | sugar alcohol | R | Y | n | m.p. |
|---|---|---|---|---|---|
| 9 | xylitol | $C_{18}H_{37}$ | 0 | 1 | 54° C |
| 10 | sorbitol | " | 0 | 2 | 54° C |
| 11 | mannitol | " | 0 | 2 | 54° C |
| 12 | dulcitol | " | 0 | 2 | 52°-53° C |
| 13 | sorbitol | industrial glycerol monostearate | 0 | 2 | 52°-53° C |
| 14 | mannitol | " | 0 | 2 | 55° C |
| 15 | dulcitol | " | 0 | 2 | 52°-53° C |
| 16 | sorbitol | $C_{18}H_{37}$ | NH | 2 | 70°-75° C |

EXAMPLES 17 to 24

Compounds of the formula

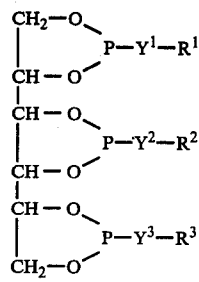

were prepared under the conditions of Example 1 by reacting 1 mol of sugar alcohol, 3 mols of triethyl phosphite and 3 mols altogether of alkyl amine, alkyl mercaptan and/or alkanol, optionally in the presence of basic catalysts.

| Example No. | sugar alcohol | $R^1$—$Y^1$—H | $R^2$—$Y^2$—H | $R^3$—$Y^3$—H | m.p.° C |
|---|---|---|---|---|---|
| 17 | sorbitol | $C_{12}H_{25}$—$NH_2$ | $C_{18}H_{37}OH$ | $C_{18}H_{37}OH$ | ~20 |
| 18 | " | $C_{18}H_{37}$—$NH_2$ | " | " | 50–53 |
| 19 | " |  | $C_{18}H_{37}$—$NH_2$ | " | 55–58 |
| 20 | " |  |  | $C_{18}H_{37}$—$NH_2$ | 70–73 |
| 21 | " | $C_{18}H_{37}$—NH—$CH_3$ | $C_{18}H_{37}OH$ | $C_{18}H_{37}OH$ | 35–40 |
| 22 | " | $(C_{18}H_{37})_2NH$ | " | " | 32–35 |
| 23 | " | $C_{12}H_{25}$—SH | " | " | 40 |
| 24 | mannitol | $C_{12}H_{25}$—SH | " | " | 45 |

EXAMPLE 25

Tristearyl-sorbityl diphosphite monophosphate

In a nitrogen current
182 g (1 mol) of sorbitol
117 ml (1 mol) of freshly distilled trimethyl phosphate
360 ml (2 mols) of triethyl phosphite,
810 g (3 mols) of stearyl alcohol and 1 ml of triethyl amine
were stirred at 120° to 200° C. until no more alcohol distilled over a 20 cm Vigreux column. The hot residue was filtered through a folded filter. 964 grams of a white solid melting at 48° to 50° C. were obtained

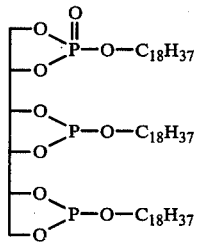

EXAMPLE 26

This example is intended to demonstrate the surprisingly high stability to hydrolysis of the phosphites of the invention.

The stability to hydrolysis was tested according to the process disclosed in DT-OS 2,144,181, pages 7/8. 5.0 g each of the respective phosphite were boiled for 20 and 60 minutes in 100 ml of deionized water. The mixture was then allowed to cool, filtered to remove residues, if any, and in the filtrate the liberated phosphorous acid was titrated with 0.1N KOH against bromophenol blue.

In the following table is indicated the degree of hydrolysis determined under the specified conditions as quotient of the actual consumption of KOH and the theoretically possible consumption with a complete hydrolysis.

TABLE I:

|  | degree of hydrolysis after | |
|---|---|---|
|  | 20 minutes | 60 minutes |
| phosphite of Example | (in % of theory) | |
| 1 | 7 | 17 |
| 2 | 5 | 10 |
| 4 | 10 | — |
| 5 | 7 | 23 |
| 8 | 7 | 11 |
| 11 | 28 | — |
| 25 | 9 | — |
| 0 |  |  |
| comparative phosphites: |  |  |
| distearyl-pentaerthrityl-diphosphite | 55 | 68 |
| triphenyl phosphite | 84 | 100 |
| trisnonylphenyl phosphite | 57 | 92 |
| di-phenyl-isooctyl-phosphite | 55 | 72 |

EXAMPLE 27

This example is intended to demonstrate the utilitarian properties of the phosphites of the invention in polyvinyl chloride. The parts in the following description are parts by weight.

Each time 100 parts of a mass polyvinyl chloride having a K value of 60 were intimately mixed with
0.2 part of 2-phenyl-indole,
3.0 parts of epoxidized soybean oil
0.25 part of a complex calcium/zinc stabilizer consisting of 42% by weight of calcium stearate, 30% by weight of zinc stearate, 22% by weight of pentaerythritol and 6% by weight of 2,6-di-tert.butyl-4-methylphenol
0.2 part of a montanic acid ester (acid number 18, esterification number 154)
0.3 part of stearyl stearate
0.5 part of glycerol monostearate and
0.5 part of the respective phosphite of the invention.

To measure the dynamic heat stability (rolling stability) the mixtures were rolled on a two roll mill at 180° C. and with 20 revolutions per minute. At intervals of 10 minutes samples were taken from the rough sheet and the color of the samples was compared with the colors of a proper color chart. Rolling was continued until the rough sheet had turned black.

In order to measure the static heat stability (furnace stability) a rough sheet was prepared as described above and the sheet was rolled for a further 10 minutes at 180° C. Flat samples having a diameter of about 30 mm were punched out of the rough sheet removed from the mill and having a thickness of about 0.5 mm, the samples were wrapped in aluminum foil and heated to 180° C. in a heating cabinet with air circulation. At intervals of 10 minutes each a sample was taken from the cabinet and the color thereof was compared with that of the color chart. In the following table the time is indicated until the sample had turned black.

In the color chart used the individual notes have the following meaning:

1 = water clear
2 = slightly yellowish
3 = intense yellow color
4 = dark yellow-brown color
5 = dark brown to black It can be seen from the following table that the phosphites of the invention give excellent results as regards the dynamic as well as the static stabilization effect and that they are distinctly superior to commercial phosphites.

Table II
Stabilization effect of the phosphites of the invention in PVC

| phosphite of Example | dynamic (rolling) stability discoloration of rough sheet after a rolling time of | | | | | | | | static (furnace) stability black coloration at 180° C after |
|---|---|---|---|---|---|---|---|---|---|
| | 10' | 20' | 30' | 40' | 50' | 60' | 70' | 80' | |
| 1 | 1 | 1–2 | 2 | 2–3 | 3 | 3 | 4 | 4 | — |
| 2 | 1 | 1–2 | 2 | 2–3 | 3 | 3 | 4 | 4 | — |
| 3 | 1 | 1–2 | 2 | 3 | 4 | 5 | — | — | 60' |
| 4 | 1 | 1–2 | 2 | 2 | 3 | 3 | 4 | 5 | — |
| 5 | 1 | 1–2 | 2 | 2 | 3 | 3 | 4 | 5 | — |
| 6 | 2 | 3 | 3 | 3 | 4 | 4 | 5 | — | 60' |
| 7 | 1 | 3 | 3 | 3 | 4 | 4 | 5 | — | 60' |
| 8 | 1 | 1–2 | 1–2 | 2 | 3 | 4 | 5 | — | 60' |
| 10 | 1 | 1–2 | 2 | 3 | 4 | 5 | — | — | 60' |
| 11 | 2 | 2–3 | 2–3 | 3 | 3 | 4 | 5 | — | 60' |
| 13 | 2 | 2–3 | 2–3 | 3 | 3–4 | 4 | 5 | — | 60' |
| 14 | 1 | 2 | 2 | 3 | 3 | 4 | 5 | — | 60' |
| 15 | 1 | 1–2 | 2 | 2–3 | 3 | 4 | 5 | — | 60' |
| 22 | 2 | 3 | 3 | 4 | 4 | 5 | — | — | 70' |
| 23 | 2 | 3 | 3 | 3 | 3–4 | 4 | 5 | — | 60' |
| Comparison: | | | | | | | | | |
| distearyl-pentaerythrityl diphosphite | 2–3 | 2–3 | 3 | 3 | 4 | 5 | — | — | 50' |
| triphenyl phosphite | 1 | 2 | 2–3 | 5 | — | — | — | — | 50' |
| trisnonyl-phenyl phosphite | 1 | 2 | 2–3 | 3 | 5 | — | — | — | 40' |
| diphenyl-isooctyl-phosphite | 1 | 2–3 | 3 | 5 | — | — | — | — | 70' |

EXAMPLE 28

This example is intended to demonstrate the stabilizing effect of the phosphites of the invention in polypropylene.

A mixture of 100 parts of unstabilized pulverulent polypropylene having a density of 0.90 (melt index $i_5$ about 6 g/10 min, determined analogous to ASTM D 1238-62 T)

0.15 part of laurin-thiodipropionic acid ester 0.10 part of bis(4'-hydroxy-3'-tert.butylphenyl)-butanoic acid ester, 0.20 part of calcium stearate and 0.30 part of a phosphite of the invention was homogenized for 5 minutes at 200° C. on a two roll mill. The molten composition was then molded at 200° C. into a sheet 1 mm thick and from the cold sheet test specimens according to DIN 53,455 were cut out.

To determine the stability to light the test specimens were exposed to the changing light of a Xenotest apparatus, type 150, by Messrs. Hanau Quarzlampen GMBH, the irradiation intensity being modulated by 6 IR filters and 1 UV window (DIN 53,387). The time of exposure in hours was measured after which the absolute elongation at break had dropped to 10% of the initial value. The elongation at break was measured in the Instrom tensile testing machine at a draw off speed of 5 cm/min. The energy of radiation absorbed per square centimeter was calculated from the time of exposure and the intensity of irradiation.

The test results are listed in the following table.

| phosphite of Example | exposure time in hours | radiation energy (KJ/cm$^2$) |
|---|---|---|
| 1 | 638 | 14.0 |
| 2 | 584 | 12.9 |
| 25 | 650 | 14.2 |
| without | 195 | 4.7 |

It can be seen that the phosphites of the invention are excellently suitable for stabilizing polyolefins.

EXAMPLE 29

This example illustrates the method used for determining the acute toxicity of the phosphites of the invention.

To test the acute toxicities of the compounds of the invention male albino mice were fed as prescribed in the book "Grundlagen der experimentellen Arzneimittelforschung" by Leopold Ther, edition 1965.

The phosphite to be tested was administered per os, suspended in aqueous methyl cellulose (Tylose ®) solution, to groups of 5 test animals each, the doses being 1,000, 2,000, and 5,000 mg/kg of body weight.

The following compounds were tested:
tristearyl-sorbityl triphosphite (Example 1)
tristearyl-mannityl triphosphite (Example 2)
distearyl-sorbityl diphosphite (Example 10) and
distearyl-monododecyl-mercapto-sorbityl triphosphite (Example 23).

With all these substances even with the highest doses none of the test animals showed any sign of poisoning or died.

What is claimed is:

1. A compound of the formula

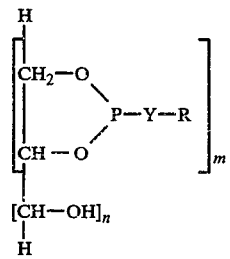

in which $m = 2$ or $3$, $n = 0$, 1 or 2 and $2m + n$ is equal to or lower than 6, $Y = -O-$, $-S-$ or $-NR'-$ with $R' = H$ or $C_1$ to $C_{20}$-alkyl, $R = $ an unbranched alkyl group, having 12 to 20 carbon atoms.

2. A compound as claimed in claim 1, wherein $2m + n$ is 6, and $Y$ is oxygen.

3. Moldable plastics composition consisting essentially of a member selected from the group of homopolymers and copolymers of halogen-free $C_2$ to $C_4$-alpha-olefins, chlorinated polyolefins and chlorine-containing vinyl homo- and copolymers and containing as stabilizer a compound as claimed in claim 1 in an amount of from 0.05 to 5.0 parts by weight per 100 parts by weight of polymer.

4. Process for stabilizing homopolymers and copolymers of halogen-free, $C_2$ to $C_4$-α-olefins, chlorinated polyolefins and chlorine-containing vinyl homo- and copolymers against the detrimental effect of light and heat, which comprises adding to the said polymers during processing from 0.05 to 5.0 parts by weight, for 100 parts by weight of polymer, of at least one compound as claimed in claim 1, optionally in admixture with other heat and light stabilizers.

5. Stabilizer combination for homopolymers and copolymers of halogen-free $C_2$ to $C_4$-α-olefins, consisting of 0.05 to 5.0 parts by weight of at least one compound as claimed in claim 1, 0.05 to 3.0 parts by weight of a known phenolic stabilizer, 0.05 to 0.2 parts by weight of a calcium salt of a fatty acid or a wax acid, 0 to 3.0 parts by weight of a known sulfidic stabilizer and 0 to 3.0 parts by weight of a known UV stabilizer.

6. Stabilizer combination for chlorinated polyolefins and chlorine-containing vinyl homo- and copolymers, consisting of 0.05 to 5.0 parts by weight of at least one compound as claimed in claim 1, 0.1 to 5.0 parts by weight of a metal soap known as stabilizer, 0.1 to 5.0 parts by weight of a known epoxide stabilizer and 0 to 1.0 part by weight of a polyhydric alcohol.

* * * * *